US009763450B2

(12) United States Patent
Roechling et al.

(10) Patent No.: US 9,763,450 B2
(45) Date of Patent: Sep. 19, 2017

(54) CHEMICAL STABILIZATION OF IODOSULFURON-METHYL SODIUM SALT BY HYDROXYSTEARATES

(71) Applicant: BAYER CROPSCIENCE AG, Monheim (DE)

(72) Inventors: Andreas Roechling, Langenfeld (DE); Ankin Akyuez, Frankfurt am Main (DE)

(73) Assignee: BAYER CROPSCIENCE AG, Monheim (DE)

( * ) Notice: Subject to any disclaimer, the term of this patent is extended or adjusted under 35 U.S.C. 154(b) by 71 days.

(21) Appl. No.: 14/401,186

(22) PCT Filed: May 22, 2013

(86) PCT No.: PCT/EP2013/060448
§ 371 (c)(1),
(2) Date: Nov. 14, 2014

(87) PCT Pub. No.: WO2013/174833
PCT Pub. Date: Nov. 28, 2013

(65) Prior Publication Data
US 2015/0105259 A1  Apr. 16, 2015

(30) Foreign Application Priority Data
May 25, 2012 (EP) .................... 12169514

(51) Int. Cl.
*A01N 25/02* (2006.01)
*A01N 47/36* (2006.01)
*A01N 25/04* (2006.01)
*A01N 25/30* (2006.01)
*A01N 25/22* (2006.01)

(52) U.S. Cl.
CPC ............ *A01N 47/36* (2013.01); *A01N 25/04* (2013.01); *A01N 25/22* (2013.01); *A01N 25/30* (2013.01)

(58) Field of Classification Search
CPC ........ A01N 47/36; A01N 25/04; A01N 25/22; A01N 25/30
See application file for complete search history.

(56) References Cited

U.S. PATENT DOCUMENTS

| 2,867,519 A * | 1/1959 | Bartlett et al. ................ 504/323 |
| 4,599,412 A | 7/1986 | Sandell |
| 4,671,817 A | 6/1987 | Wexler |
| 4,683,000 A | 7/1987 | Petersen |
| 6,479,432 B1 | 11/2002 | Sixl |
| 2004/0097378 A1* | 5/2004 | Maier .................... A01N 25/02 504/363 |
| 2005/0026787 A1 | 2/2005 | Deckwer et al. |
| 2005/0032647 A1 | 2/2005 | Deckwer et al. |
| 2005/0233906 A1 | 10/2005 | Schnabel et al. |
| 2010/0130364 A1* | 5/2010 | Casana Giner et al. ...... 504/133 |

FOREIGN PATENT DOCUMENTS

| EP | 163598 A1 | 12/1985 |
| EP | 245058 A2 | 11/1987 |
| EP | 0313317 A2 | 4/1989 |
| EP | 0514769 A1 | 11/1992 |
| EP | 0554015 A1 | 8/1993 |
| EP | 764404 A | 8/1993 |
| WO | 9313658 A1 | 7/1993 |
| WO | 9834482 A | 8/1998 |
| WO | 0130156 A1 | 5/2001 |
| WO | 0182693 A2 | 11/2001 |
| WO | 2004054364 A1 | 7/2004 |
| WO | 2005051082 A1 | 6/2005 |

OTHER PUBLICATIONS

International Search Report from corresponding PCT/EP2013/060448, mailed Jun. 19, 2013.

* cited by examiner

*Primary Examiner* — David Browe
(74) *Attorney, Agent, or Firm* — McBee Moore Woodward & Vanik IP, LLC; Susan McBee; David Woodward

(57) ABSTRACT

A formulation in the form of an oil dispersion includes as agrochemical active ingredient iodosulfuron-methyl sodium salt, one or more hydroxystearates, at least one emulsifier, at least one plant oil or mineral oil or an ester of a plant oil or mineral oil, and optionally auxiliaries and additives.

15 Claims, No Drawings

CHEMICAL STABILIZATION OF IODOSULFURON-METHYL SODIUM SALT BY HYDROXYSTEARATES

CROSS REFERENCE TO RELATED APPLICATIONS

This application is a §371 National Stage Application of PCT/EP2013/060448, filed May 22, 2013, which claims priority to EP 12169514.2, filed May 25, 2012.

BACKGROUND

Field of the Invention

The present invention relates to novel oil dispersion formulations (OD formulations) of iodosulfuron-methyl sodium salt which comprise hydroxystearates, in particular lithium hydroxystearate. Iodosulfuron-methyl sodium salt is a herbicidal active ingredient from the group of sulfonamides, in particular sulfonylureas.

Description of Related Art

Active ingredients for crop protection are generally not used in their pure form. Depending on the field of application and the type of application, and also on physical, chemical and biological parameters, the active ingredient is used in a mixture with customary auxiliaries and additives as active ingredient formulation. The combinations with other active ingredients for extending the spectrum of action and/or for protecting crop plants (e.g. by safeners, antidotes) are also known.

Formulations of active ingredients for crop protection should generally have high chemical and physical stability, good applicability and user friendliness and a broad biological effect with high selectivity.

Herbicidal active ingredients from the group of sulfonamides, such as sulfonylureas, generally have a high degree of chemical reactivity and tend towards chemical degradation, e.g. as a result of hydrolysis.

One option of formulating chemically labile active ingredients is the production of solid formulations. Thus, formulations of active ingredients from the group of sulfonylureas are known in the form of powders, granules and tablets (e.g. in EP A 764404, WO A 1998/34482, WO A 1993/13658). The processes for producing solid formulations, e.g. in the form of granules and tablets, however, are generally laborious, particularly if low-melting active ingredients or auxiliaries and additives are incorporated. Moreover, solid formulations are generally more difficult to apply and less user-friendly.

Liquid formulations are in most cases easier to apply, are more user-friendly and moreover generally exhibit better biological efficacy.

Liquid formulations of sulfonylureas are described e.g. in U.S. Pat. No. 4,599,412, U.S. Pat. No. 4,683,000, U.S. Pat. No. 4,671,817, EP A 245058, WO A 2001/82693, EP A 0313317, EP A 0514768, EP A 163598 and EP A 0514769.

The object of providing an improved crop protection composition formulation with the chemically very reactive sulfonylureas which has high chemical stability as well as high biological effectiveness and crop plant tolerability was described by the patent application WO A 2004/054364.

In addition, the use of sulfosuccinates as auxiliary is described in WO A 2004/054364. Sulfosuccinates are in the meantime used in most oil dispersion formulations of sulfonylureas and effect the chemical stabilization of the sulfonylureas.

Since the often used dioctylsulfosuccinate sodium salt has the classification R 41 (risk of serious damage to eyes) according to EU Guideline 67/548/EEC or 1999/45/EC, further, more user-friendly alternatives have been sought for the chemical stabilization of sulfonylureas.

Additionally, the oil dispersions are generally thickened with sheet silicates in order to prevent phase separations and settling of solid particles. The components hitherto used most frequently for this are the Bentone grades Bentone 34® and Bentone 38® from Elementis GmbH based on montmorillonite. However, these very frequently have a tendency toward uncontrolled considerable thickenings, which can make it difficult to empty the trade packs.

Moreover, the use of hydroxystearates as thickeners is known from the lubricant industry. A use of stearates in agrochemical formulations, however, has hitherto not been described.

It has now been found that when using hydroxystearates as thickeners in oil-based liquid formulations of iodosulfuron-methyl sodium salt the hydroxystearate surprisingly also brings about, as well as the thickening, a chemical stabilization of the sulfonylureas.

In particular, the lithium hydroxystearate exhibited a particularly significantly stabilizing effect on the sodium salt of iodosulfuron.

SUMMARY

The invention relates to formulations in the form of an oil dispersion comprising
- as agrochemical active ingredient iodosulfuron-methyl sodium salt,
- one or more hydroxystearates and
- at least one emulsifier and
- at least one plant oil or mineral oil or an ester of a plant oil or mineral oil and
- optionally further auxiliaries and additives.

Preferably, the invention relates to formulations in the form of an oil dispersion comprising
- 0.01 to 10% by weight, preferably 0.1 to 5% by weight, based on the weight of the formulation, of iodosulfuron-methyl sodium salt, and
- 0.01 to 10% by weight, preferably 0.1 to 5% by weight, based on the weight of the formulation, of one or more hydroxystearates and
- 0.1 to 20% by weight, preferably 1 to 15% by weight, based on the weight of the formulation, of one or more emulsifiers and
- 50 to 99% by weight, preferably 55 to 95% by weight, based on the weight of the formulation, of one or more plant or mineral oils or esters of one or more plant or mineral oils and
- optionally further auxiliaries and additives.

Here, the fractions by weight in % by weight refer, in the event of the presence of two or more hydroxystearates, emulsifiers or oils or esters thereof in the formulation according to the invention, in each case to the total of the hydroxystearates, emulsifiers or oils or esters thereof.

The formulations according to the invention are anhydrous, i.e. their water content is less than 1% by weight, based on the weight of the formulation.

DETAILED DESCRIPTION OF A PREFERRED EMBODIMENT

In a preferred embodiment of the invention, the hydroxystearate used is lithium hydroxystearate. However, it is likewise possible to use other hydroxystearates, such as, for example, sodium hydroxystearate, calcium hydroxystearate or zinc hydroxystearate.

The invention also relates to a process for the preparation of the formulations according to the invention, in which the sodium salt of iodosulfuron-methyl is finely dispersed together with the emulsifier in the plant or mineral oil or in the ester of a plant or mineral oil and then the hydroxystearate and optionally further auxiliaries and additives are added.

The invention also relates to a process for the preparation of the formulations according to the invention, in which the sodium salt of iodosulfuron-methyl is finely dispersed together with the emulsifier, the hydroxystearate and optionally further auxiliaries and additives in the plant or mineral oil or in the ester of a plant or mineral oil.

The invention also relates to the use of the formulations according to the invention for controlling weeds. Preferably, for this purpose, the formulations according to the invention are diluted with water, thus producing a crop protection composition which can then be used for controlling undesired plant growth.

The invention also relates to a method for controlling undesired plant growth, in which the formulation according to the invention or the crop protection composition according to the invention is applied to the harmful plants (weeds), plant parts, plant seeds or the area on which the plants grow.

Preferably, the formulations according to the invention comprise iodosulfuron-methyl sodium salt as the sole active ingredient. However, it is likewise possible to use, in addition to iodosulfuron-methyl sodium salt, one or more further agrochemical active ingredients and/or safeners in the formulation according to the invention.

Suitable further agrochemical active ingredients are in particular 2,4-D-2-ethylhexyl ester, amidosulfuron sodium salt, diflufenican, flufenacet, fenoxaprop-P-ethyl, foramsulfuron sodium salt, indaziflam, isoxaflutole, metribuzin, mesosulfuron-methyl sodium salt, propoxycarbazone sodium salt, pyrasulfotole, tembotrione, thiencarbazone-methyl, triafamone.

Suitable safeners are in particular cyprosulfamide, isoxadifen-ethyl, mefenpyr-diethyl.

Preferably, the formulations according to the invention comprise lithium hydroxystearate, particularly preferably lithium 12-hydroxystearate. Preferably, the formulations according to the invention comprise lithium hydroxystearate as the sole hydroxystearate.

Preferred nonionic emulsifiers and dispersants are e.g. alkoxylated alcohols, alkoxylated fatty acids, alkoxylated triglycerides which contain hydroxy fatty acids, polyethyleneoxide-polypropyleneoxide block copolymers and alkylphenol alkoxylates.

Preferred ionic emulsifiers/dispersants are e.g. salts of alkylarylsulfonic or phosphonic acids and polyelectrolytes from the polycondensation of naphthalenesulfonate and formaldehyde.

Preferred plant oils or esters of plant oils are soybean oil, rapeseed oil, corn seed oil, sunflower oil, cotton seed oil, linseed oil, coconut oil, palm oil, safflower oil, walnut oil, peanut oil, olive oil or castor oil, in particular rapeseed oil.

The fatty acid esters are preferably esters of C10-C22, preferably C12-C20 fatty acids. The C10-C22 fatty acid esters are for example esters of unsaturated or saturated C10-C22 fatty acids, in particular with an even number of carbon atoms, e.g. erucic acid, lauric acid, palmitic acid and in particular C18 fatty acids such as stearic acid, oleic acid, linoleic acid or linolenic acid.

Rapeseed oil methyl ester is particularly preferred.

Preferred mineral oils are mixtures of aromatic and aliphatic hydrocarbons, such as solvents of the Solvesso® series, e.g. Solvesso®100, Solvesso®150 or Solvesso®200 (ExxonMobil Chemicals), of the Solvarex®/Solvaro® series (TotalFinaElf) or of the Caromax® series, e.g. Caromax®28 (Petrochem Carless).

Solvesso® 200 and Solvesso® 200 ND are particularly preferred.

The plant oils or mineral oils or esters thereof can be present on their own or in a mixture. The oils used preferably have a low dissolving power for the agrochemical active ingredient or ingredients used, in particular the phenylsulfonamides.

Besides the surfactants such as emulsifiers and dispersants, thickeners and thixotropic agents, wetting agents, anti-drift agents, adhesives, penetration agents, preservatives and frost protection agents, antioxidants, solubility promoters, fillers, carriers and dyes, antifoams, fertilizers, evaporation inhibitors, as well as agents that influence the pH and the viscosity are preferred auxiliaries and additives.

The formulations according to the invention have excellent herbicidal efficacy against a broad spectrum of economically important mono- and dicotyledonous annual harmful plants. Difficult-to-control perennial harmful plants which emerge from rhizomes, rootstocks and other permanent organs are also easily tackled by the formulations.

The present invention therefore also provides a method for controlling undesired plants or for regulating the growth of plants, preferably in crop cultures, in which a formulation according to the invention or a crop protection composition prepared therefrom (preferably application mixtures such as e.g. spray mixtures) are applied to the plants (e.g. harmful plants such as mono- or dicotyledonous weeds or undesired crop plants), the seed material (e.g. grains, seeds or vegetative replication organs such as tubers or sprouting parts with buds) or the area on which the plants grow (e.g. the cultivated area). In this connection, the formulations according to the invention or the crop protection compositions prepared therefrom can be applied e.g. prior to sowing (optionally also by incorporation into the soil), pre-emergence or post-emergence. Specifically, some representatives of the mono- and dicotyledonous weed flora which can be controlled by the formulations according to the invention or a crop protection composition prepared therefrom may be mentioned by way of example, although the naming is not intended to constitute a restriction to certain species.

Monocotyledonous harmful plants of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Dicotyledonous weeds of the genera: *Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola,*

Senecio, Sesbania, Sida, Sinapis, Solanum, Sonchus, Sphenoclea, Stellaria, Taraxacum, Thlaspi, Trifolium, Urtica, Veronica, Viola, Xanthium.

When the compounds according to the invention are applied to the soil surface before germination, either the weed seedlings are prevented completely from emerging or the weeds grow until they have reached the cotyledon stage, but then stop growing and eventually, after three to four weeks have elapsed, die completely.

If the formulations or the crop protection compositions prepared therefrom are applied post-emergence to the green parts of the plants, growth stops after the treatment, and the harmful plants remain at the growth stage at the time of application, or they die completely after a certain time, so that in this manner competition by the weeds, which is harmful to the crop plants, is eliminated very early and in a lasting manner.

Moreover, the formulations according to the invention or a crop protection composition prepared therefrom have (depending on the application rate applied) excellent growth-regulating properties in crop plants. They intervene in the plants' own metabolism with regulatory effect, and can thus be used for the targeted influencing of plant ingredients and to facilitate harvesting, such as e.g. by triggering desiccation and stunted growth. Furthermore, they are also suitable for the general control and inhibition of unwanted vegetative growth without killing the plants in the process. An inhibition of the vegetative growth plays a major role for many mono- and dicotyledonous plants since, for example, this can reduce or completely prevent lodging.

On account of their herbicidal and plant-growth-regulatory properties, the formulation or a crop protection composition prepared therefrom can also be used for controlling harmful plants in crops of genetically modified plants or plants modified by conventional mutagenesis. In general, transgenic plants are characterized by particular advantageous properties, for example by resistances to certain pesticides, in particular certain herbicides, resistances to plant diseases or pathogens of plant diseases, such as certain insects or microorganisms such as fungi, bacteria or viruses. Other particular properties relate e.g. to the harvested material with regard to quantity, quality, storeability, composition and specific constituents. For example, transgenic plants with an increased starch content or altered starch quality, or those with a different fatty acid composition of the harvested material are known.

As regards transgenic cultures, preference is given to the use of the compounds according to the invention in economically important transgenic cultures of useful plants and ornamentals, e.g. of cereals such as wheat, barley, rye, oats, millet, rice and corn, or else crops of sugar beet, cotton, soybean, rapeseed, potato, tomato, peas and other types of vegetable.

Preferably, the compounds according to the invention can be used as herbicides in crops of useful plants which are resistant, or have been made resistant by genetic engineering, to the phytotoxic effects of the herbicides.

The examples listed below (tables 1-9) show the chemical stabilization of the sodium salt of iodosulfuron-methyl by lithium hydroxystearate.

PREPARATION EXAMPLES

The sodium salt of iodosulfuron-methyl (iodosulfuron-methyl-sodium, IMS) is finely dispersed by means of a rotor-stator mixer together with a customary emulsifier such as Emulsogen EL 400® (castor oil polyglycol ether from Clariant AG) in the solvents customary for OD formulations (oil dispersion formulations), such as rapeseed oil methyl ester or Solvesso 200 ND® (aromatics mixture from Exxon AG). Further formulation auxiliaries such as the thickener Bentone 38® (sheet silicate from Elementis AG) or the polymers Ligalub PEG 400 MO® (polyethylene glycol monooleate from Peter Greven GmbH), Ligalub 12 GE® (glyceryl dioleate from Peter Greven GmbH) or Ligalub 71 KE® (complex ester from Peter Greven GmbH) can, inter alia, also be added to the system. Furthermore, lithium hydroxystearate (lithium soap of a 12-hydroxystearic acid) was also additionally added for comparison purposes to each mixture.

Tables 1 to 9 show the compositions of the tested OD formulations (% data in % by weight).

The degradation of the IMS is determined here by means of HPLC.

The degradation is expressed here in tables 1 to 9 in—xx %. This means that after the relevant period xx % of the originally present IMS was already degraded.

In all of the systems listed, the degradation of the sodium salt of iodosulfuron following storage at various storage temperatures and for various storage times has significantly reduced as a result of the addition of lithium hydroxystearate.

TABLE 1

| | | |
|---|---|---|
| Iodosulfuron-methyl-sodium (IMS) | 0.5% | 0.5% |
| Emulsogen EL 400 | 10% | 10% |
| Lithium hydroxystearate | 0% | 1% |
| Bentone 38 | 1.2% | 1.2% |
| Rapeseed oil methyl ester | 88.3% | 87.3% |
| Degradation of IMS after 1 week at 54° C. | −78.3% | −23.9% |
| Degradation of IMS after 4 weeks at 40° C. | −46.4% | −5% |
| Degradation of IMS after 8 weeks at 40° C. | −69.7% | −8.7% |
| Degradation of IMS after 12 weeks at 35° C. | −57.8% | −6.3% |

TABLE 2

| | | | | |
|---|---|---|---|---|
| Iodosulfuron-methyl-sodium (IMS) | 0.5% | 0.5% | 0.5% | 0.5% |
| Emulsogen EL 400 | 10% | 10% | 10% | 10% |
| Lithium hydroxystearate | 0% | 0.5% | 1% | 5% |
| Solvesso 200 ND | 89.5% | 89% | 88.5% | 84.5% |
| Degradation of IMS after 2 weeks at 54° C. | −87.9% | −32.2% | −28% | −14.7% |
| Degradation of IMS after 4 weeks at 40° C. | −29.9% | −7.4% | −3.4% | −3.6% |

TABLE 3

| | | |
|---|---|---|
| Iodosulfuron-methyl-sodium (IMS) | 2% | 2% |
| Emulsogen EL 400 | 10% | 10% |
| Lithium hydroxystearate | 0% | 1% |
| Solvesso 200 ND | 88% | 87% |
| Degradation of IMS after 2 weeks at 54° C. | −34.6% | −13.1% |
| Degradation of IMS after 4 weeks at 40° C. | −5.2% | −0.2% |

TABLE 4

| | | |
|---|---|---|
| Iodosulfuron-methyl-sodium (IMS) | 0.5% | 0.5% |
| Emulsogen EL 400 | 10% | 10% |
| Lithium hydroxystearate | 0% | 1% |

TABLE 4-continued

| | | |
|---|---|---|
| Ligalub PEG 400 MO | 15% | 15% |
| Solvesso 200 ND | 74.5% | 73.5% |
| Degradation of IMS after 2 weeks at 54° C. | −93.2% | −37.8% |
| Degradation of IMS after 4 weeks at 40° C. | −34.9% | −7.2% |

TABLE 5

| | | |
|---|---|---|
| Iodosulfuron-methyl-sodium (IMS) | 0.5% | 0.5% |
| Emulsogen EL 400 | 10% | 10% |
| Lithium hydroxystearate | 0% | 1% |
| Ligalub PEG 400 MO | 30% | 30% |
| Bentone 38 | 1.2% | 1.2% |
| Rapeseed oil methyl ester | 58.3% | 57.3% |
| Degradation of IMS after 2 weeks at 54° C. | −87.4% | −45.8% |
| Degradation of IMS after 4 weeks at 40° C. | −51.6% | −14.8% |
| Degradation of IMS after 8 weeks at 40° C. | −77.2% | −21% |
| Degradation of IMS after 12 weeks at 35° C. | −66.8% | −13.6% |

TABLE 6

| | | |
|---|---|---|
| Iodosulfuron-methyl-sodium (IMS) | 2% | 2% |
| Emulsogen EL 400 | 10% | 10% |
| Lithium hydroxystearate | 0% | 1% |
| Ligalub PEG 400 MO | 15% | 15% |
| Solvesso 200 ND | 73% | 72% |
| Degradation of IMS after 2 weeks at 54° C. | −81.8% | −32.7% |
| Degradation of IMS after 4 weeks at 40° C. | −32.9% | −3.2% |

TABLE 7

| | | |
|---|---|---|
| Iodosulfuron-methyl-sodium (IMS) | 0.5% | 0.5% |
| Emulsogen EL 400 | 10% | 10% |
| Lithium hydroxystearate | 0% | 1% |
| Ligalub 12 GE | 30% | 30% |
| Bentone 38 | 1.2% | 1.2% |
| Rapeseed oil methyl ester | 58.3% | 57.3% |
| Degradation of IMS after 1 week at 54° C. | −42.4% | −11.8% |
| Degradation of IMS after 4 weeks at 40° C. | −76.6% | −3.6% |
| Degradation of IMS after 8 weeks at 40° C. | −65.9% | −4.7% |
| Degradation of IMS after 12 weeks at 35° C. | −55.7% | −5.3% |

TABLE 8

| | | |
|---|---|---|
| Iodosulfuron-methyl-sodium (IMS) | 0.5% | 0.5% |
| Emulsogen EL 400 | 10% | 10% |
| Lithium hydroxystearate | 0% | 1% |
| Ligalub 71 KE | 15% | 15% |
| Solvesso 200 ND | 74.5% | 73.5% |
| Degradation of IMS after 2 weeks at 54° C. | −66.6% | −9.86% |
| Degradation of IMS after 4 weeks at 40° C. | −65% | −5.6% |

TABLE 9

| | | |
|---|---|---|
| Iodosulfuron-methyl-sodium (IMS) | 0.5% | 0.5% |
| Emulsogen EL 400 | 10% | 10% |

TABLE 9-continued

| | | |
|---|---|---|
| Lithium hydroxystearate | 0% | 1% |
| Ligalub 71 KE | 30% | 30% |
| Bentone 38 | 1.2% | 1.2% |
| Rapeseed oil methyl ester | 58.3% | 57.3% |
| Degradation of IMS after 1 week at 54° C. | −75.8% | −11.4% |
| Degradation of IMS after 4 weeks at 40° C. | −39.6% | −2.3% |
| Degradation of IMS after 8 weeks at 40° C. | −63.6% | −3% |
| Degradation of IMS after 12 weeks at 35° C. | −54.6% | −3% |

The invention claimed is:

1. A formulation in the form of an oil dispersion comprising
   as agrochemical active ingredient iodosulfuron-methyl sodium salt,
   lithium hydroxystearate,
   at least one emulsifier,
   at least one plant oil or mineral oil or an ester of a plant oil or mineral oil, and
   optionally one or more auxiliaries and additives.

2. The formulation in the form of an oil dispersion of claim 1, comprising
   0.01 to 10% by weight of the iodosulfuron-methyl sodium salt,
   0.01 to 10% by weight of lithium hydroxystearate in total,
   0.1 to 20% by weight of the at least one emulsifier in total,
   50 to 99% by weight of the at least one plant or mineral oil or the ester of a plant or mineral oil in total, and
   optionally the one or more auxiliaries and additives.

3. A process for preparing the formulation of claim 1, comprising
   dispersing the sodium salt of iodosulfuron-methyl together with the emulsifier in the plant or mineral oil or in the ester of a plant or mineral oil, and then
   adding the lithium hydroxystearates and optionally one or more auxiliaries and additives.

4. A process for preparing the formulation of claim 1, comprising dispersing the sodium salt of iodosulfuron-methyl together with the emulsifier, the lithium hydroxystearate and optionally one or more auxiliaries and additives in the plant or mineral oil or in the ester of a plant oil or mineral oil.

5. A crop protection composition obtained by diluting the formulation of claim 1 with water.

6. The formulation of claim 1 capable of being used for controlling undesired plant growth.

7. A method for controlling undesired plant growth, comprising applying the formulation of claim 1 to one or more harmful plants, one or more plant parts, one or more plant seeds and/or an area on which a plant grows.

8. The formulation of claim 2, comprising 0.1 to 5% by weight of the iodosulfuron-methyl sodium salt and 0.1 to 5% by weight of lithium hydroxystearate.

9. The formulation of claim 1, comprising a plant oil comprising a rapeseed oil methyl ester.

10. The formulation of claim 1, wherein the at least one emulsifier comprises a castor oil polyglycol ether.

11. The formulation of claim 1, comprising the one or more auxiliaries and additives and which are selected from the group consisting of a sheet silicate, a polyethylene glycol monooleate, a glyceryl dioleate, and a complex ester.

12. The formulation of claim 2, comprising the one or more auxiliaries and additives and which are selected from the group consisting of a sheet silicate, a polyethylene glycol monooleate, a glyceryl dioleate, and a complex ester.

13. The process of claim 3, comprising
    dispersing 0.1 to 5% by weight of the iodosulfuron-methyl sodium salt, and then
    adding 0.1 to 5% by weight of lithium hydroxystearate.

14. The process of claim 4, comprising dispersing 0.1 to 5% by weight of the iodosulfuron-methyl sodium salt with 0.1 to 5% by weight of lithium hydroxystearate.

15. The method of claim 7, wherein the formulation comprises 0.1 to 5% by weight of the iodosulfuron-methyl sodium salt and 0.1 to 5% by weight of lithium hydroxystearate.

* * * * *